United States Patent [19]

McLaughlin et al.

[11] 4,173,221

[45] Nov. 6, 1979

[54] EKG CABLE MONITORING SYSTEM

[75] Inventors: Richard J. McLaughlin, Hawthorne, Calif.; Wallace J. Rogozinski, 26 Dragonfly, Irvine, Calif. 92714

[73] Assignee: Wallace Rogozinski, Irvine, Calif.

[21] Appl. No.: 920,740

[22] Filed: Jun. 30, 1978

Related U.S. Application Data

[63] Continuation-in-part of Ser. No. 787,976, Apr. 15, 1977, abandoned.

[51] Int. Cl.² ............................................. A61N 1/36
[52] U.S. Cl. ................................................ 128/696
[58] Field of Search ..................... 128/2.06 B, 2.06 E, 128/2.06 R, 2.1 A, 2.1 B, 2.1 P

[56] References Cited

U.S. PATENT DOCUMENTS

| | | | |
|---|---|---|---|
| 3,690,313 | 9/1972 | Weppner et al. | 128/2.06 B |
| 3,757,778 | 9/1973 | Graham | 128/2.06 R |
| 3,868,948 | 3/1975 | Gragtz | 128/2.06 B |
| 3,910,257 | 10/1975 | Fletcher et al. | 128/2.06 R |
| 3,915,154 | 10/1975 | Cosentino | 128/2.06 B |
| 4,027,663 | 6/1977 | Fischler | 128/2.06 R |
| 4,066,974 | 1/1978 | Reinhard | 128/2.06 B |

*Primary Examiner*—William E. Kamm
*Attorney, Agent, or Firm*—Fulwider, Patton, Rieber, Lee & Utecht

[57] ABSTRACT

An EKG cable assembly includes monitoring circuitry for ascertaining whether a plurality of test leads, including a plurality of signal leads and at least one reference lead, are properly connected and operating. One embodiment of the circuitry includes a light emitting diode display differentially driven by amplifiers which continuously monitor test leads affixed to the skin of a patient. The monitoring circuitry and light emitting diode displays are housed in a cable connector that joins the test leads to a multiconductor cable leading to the EKG unit. The EKG monitoring circuitry in the cable connector verifies the integrity of a path of conductivity across the skin of the patient between signal and reference leads and detects any open circuit condition.

8 Claims, 2 Drawing Figures

EKG CABLE MONITORING SYSTEM

This is a continuation in part of U.S. Pat. application Ser. No. 787,976, filed on Apr. 15, 1977 and now abandoned.

BACKGROUND OF THE INVENTION

1. Field of the Invention

This present invention relates generally to cable monitors and, more particularly, to cable monitoring devices for concurrently monitoring the operation of a plurality of test leads, including both signal and reference leads.

2. Description of the Prior Art

In the use of electrocardiogram equipment, a patient monitoring system is typically arranged to utilize a multiconductor cable which extends from the EKG unit to the vicinity of the patient. By means of a cable connector, the wires within the multiconductor cable are connected to the skin of the patient via individual test leads. The test leads include a plurality of signal leads and usually a single reference lead. The test leads are attached to the patient by means of adhesive pads with or without snap-on connections for the test leads. The pads themselves include electrodes which contact the patient's skin. With each heartbeat of the patient, the skin condition of the patient's body causes a very small interchange of electrons between the signal lead and reference lead electrodes. This produces a very tiny signal in the test leads. In conventional systems, this signal, generated at the surface of the patient's skin, is used as a biasing signal to influence the magnitude of a larger externally generated electrical signal which is shaped and propogated to drive a CRT or pen recorder display.

A number of problems can arise between detection of a heartbeat by the test leads before a resulting signal arrives at the EKG unit. For example, the adhesive electrode pads attached to the patient may not be placed properly to receive the relatively small voltages generated. Also, the test leads are typically made of relatively fine wire to enhance their flexibility and can be broken within the overlying insulation without detection. Furthermore, the plugs and jacks used to connect the test leads to the connector are quite small and also may not make proper contact.

While these problems may occur with the test leads and pads, normally the cable connector and the multiconductor cable leading to the EKG unit itself have a relatively high degree of reliability and problems do not usually occur with the cable and connector. But, when the display on the EKG unit indicates improper electrical connections, there is usually no way to determine which test lead assembly is at fault without undue manual manipulation and examination of the test leads. Thus, there has been a need in the application of EKG units for a method of detecting faults arising in the test lead assemblies.

Conventional cable integrity checking systems have been devised to warn of any break or disconnection of the test leads. Such conventional systems employ an externally generated pulse, of low level, so as not to harm the patient, which is directed to the adhesive pad on one of a pair of test leads. These externally generated signals are produced at a high frequency, as contrasted with the rate of normal heartbeat, so that when a heartbeat occurs and the electrical condition of the skin is altered accordingly, the artifically and externally generated signal is altered according to the electrical condition of the patient's skin. That is, the external signal is amplified by the signal generated at the patient's skin and returned on one of a pair of test leads.

All present systems devised for this purpose have certain fundamental deficiencies. In particular, they all require the external generation of electrical pulses which are perodically gated to the electrode pad, reshaped by the electrical condition of the skin, passed through threshold detectors, and used as gating signals to generate an output to the CRT of the EKG. As a consequence, there is no continuous monitoring of the condition of the patient since the externally generated pulses are periodically gated through on the test leads. Also, an electrical path exists which, though protected, nevertheless is suitable to conduct inordinately large voltage pulses to the patient's skin, when malfunctions occur, and impress inordinately large voltages on the test leads.

SUMMARY OF THE INVENTION

The present invention provides continuous monitoring of the connections of the electrodes to the patient's skin, and continuous monitoring of the integrity of electrical circuits to the EKG. Utilizing the device of the present invention, there is no necessity for the generation of external pulses which are amplified and shaped by the minute electron transfer that occurs at the skin of the patient. Rather, the device of the present invention is sensitive enough to continuously monitor for the occurrence of these small electron transfers and to detect them as very small voltage pulses. Conventional cable monitoring systems are sensitive to a threshold level of approximately 350 microvolts. This is insufficient to reliably detect the small electrical pulses that are produced at the surface of the patient's skin, especially if the patient is in intensive care or convalescing. The device of the present invention, on the other hand, is sufficiently sensitive to reliably and consistently monitor and detect voltages of this level. The cable monitoring system of the present invention is consistently sensitive to a level as low as 100 microvolts. Voltages produced at skin surfaces normally reach this low level in patients who are slightly debilitated. Accordingly, the monitoring device of the present invention is ideally utilized with EKG systems which monitor patients in hospital intensive care wards, although it may also be used in emergency room situations.

A very significant feature of the present invention is that by not resorting to the generation of external pulses, and amplifying or reshaping such pulses in accordance with the much smaller voltage signals generated at the patient's skin as in conventional devices, the device of the present invention allows the EKG monitor to look at the actual pulse occuring at the patient's skin as a result of a heartbeat. This means that it is the actual pulse, and not some triggered output, which appears at the output of the EKG. Accordingly, no artifical simuli are necessary to accent the pulse resulting from the patient's heartbeat. This means that it is unnecessary, according to the present invention, to insert a voltage and current into the body of the patient. This feature eliminates the ever present risk of electrocution by the monitoring system, since voltage and current flowing toward the patient are completely blocked.

Another advantage that results by amplifying only the pulse generated at the surface of the patients skin is that the shape of the pulse, once amplified, is meaningful for diagnostic purposes. When an artifical pulse is employed and amplified by the pulse evolving from the patient's heartbeat, as has heretofore been done, the pulse shape is meaningless since it is largely dictated by the external pulse generating circuitry. However, pulses derived from the EKG monitoring cable utilizing the present invention reflect the strength and timing of heart valve operation indicated by the r-s-t pattern which is displayed or imprinted on the EKG. Medical diagnosis from this pattern is therefore possible, since pursuant to the present invention, no pulse shaping network is necessary. Rather, the pulses are taken directly from the patient, amplified and displayed.

Another feature of the invention is the differentially driven amplifying network. In association with each pair of electrode leads, a primary pair of differential amplifiers are driven in parallel. One input to one of these differential amplifiers is from the reference electrode lead that is connected to the patient's skin. Another input is to the other differential amplifier from a signal electrode. Once the electrodes are connected to the patient's skin, however, a Helmoholz layer tends to build up to reduce the pulse amplitude on the signal lead, relative to the reference lead. Compensation is achieved according to the present invention, however, by providing a floating ground between the two differential amplifiers. Thus, a common bias or potential is applied to both of the differential amplifiers in opposition to provide this compensation.

The outputs of the pair of differential amplifiers in the primary stage are directed in opposition to the inputs of a subsequent differential amplifier in a secondary amplification stage. By means of this connection, and because of the low voltage signals elicited from the patient, the EKG monitoring cable is not susceptible to the influence of 60 cycle a.c. noise. Such electrical noise is present in the air in environments wherever conventional a.c. line current flows. Because inductive forces of the 60 cycle a.c. current present in the vicinity influence both of the differential amplifiers of the primary amplifier stage to an equal extent and with opposite polarity, the outputs of each of these differential amplifiers to the secondary stage compensate for any ambient 60 cycle influence.

A further advantage of the present invention is that no threshold detection is required. In conventional EKG monitoring connectors, some form of threshold detection is normally provided. This is because a relatively large externally generated pulse is employed. The appearance of smaller extraneous pulses would lead to the erroneous amplification of noise signals in the absence of threshold detection. However, because the present invention operates upon signals that are sensitive 200 microvolts or more below the level of conventional heartbeat signals, threshold detection is neither necessary nor desirable. Rather, the dual differential amplifiers in each primary stage, running in opposition to each other compensate for noise that appears in the circuit. Noise is amplified equally in the differential amplifiers of the primary stage, but the amplified noise signals cancel each other out.

The present invention also provides input filtering. The noise appearing on the signal leads is filtered by a resistor-capacitor circuit located before the dual differential amplifiers in the primary stage and before amplification of the signal for a visual display in the secondary stage. The inputs to the primary amplifiers are all a.c. coupled, while the outputs therefrom to the secondary stage are d.c. coupled. The primary amplifier feedback circuits are interconnected so that any drift in one amplifier is offset by a counteracting feedback input to the other. All amplifiers employed are differential amplifiers. Moreover, there is a very high impedance coupling into the amplifiers of the primary stage to obtain minimum loading effects.

An additional feature of the present invention is the voltage clamping circuit between the test leads and a floating ground in the monitor. Because the signals received from the patient are so small, the clamping circuit can be set quite low, so that no inordinately large voltages can be transmitted to the patient, should some equipment malfunction occur.

An EKG monitoring cable of the present invention provides a means for determining the proper connection and operation of the test leads by providing individual indicating displays such as light emitting diodes for each signal lead. The presence of a signal voltage entering the cable connector from each signal lead is indicated by illumination of a light emitting diode associated therewith. The LED display itself monitors for an open circuit condition. This may be caused by broken test leads or bad connections of the electrodes to the patient's skin.

If a test lead assembly is properly operating, the LED display for each signal lead will blink on with the occurrence of each heartbeat. If there is a break in any test lead between the patient and the cable monitor, or a bad electrode connection in an adhesive pad coupled to one of the test leads, the LED associated with the signal lead or leads affected will remain on continuously. If there is a break in the test lead connections in the cable between the cable connector of the invention and the EKG display, no CRT trace will appear on the EKG monitor, although the lights in the cable connector of the invention will still be blinking. If the ground connection for the cable connector is bad, all lights will be illuminated continuously. If the patient's heartbeat ceases, all lights in the cable connector will be extinguished.

The various features of the EKG cable monitoring system of the present invention will become readily apparent from the following detailed description.

DESCRIPTION OF THE PREFERRED EMBODIMENT

Figure 1:
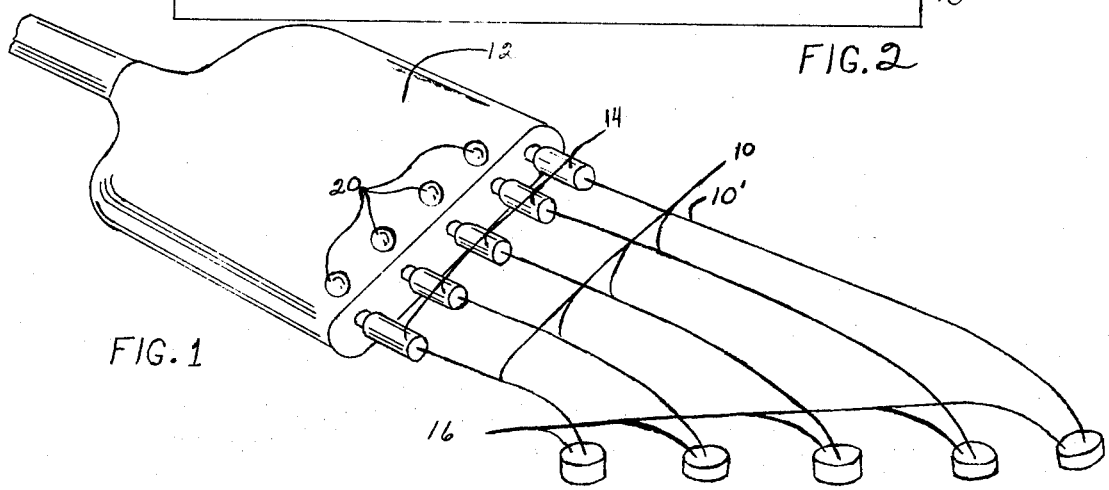
FIG. 1 is a diagrammatic perspective view of an EKG monitor cable with the LED displays shown on the cable connector.

Turning now to the drawings, the structure of the EKG cable monitoring system is depicted in FIG. 1 and is housed in a flattened plastic cable connector 12. From one end of the cable connector 12, a plurality of pairs of EKG leads are encompassed within a flexible cable 15 that extends to an EKG monitor. The monitor may be of any conventional type, including CRT displays, pen recorders, and other types of cardiac monitors that are typically used in hosiptal emergency rooms and intensive care wards.

At the opposite end of the cable connector 12, a plurality of plug connections 14 extend outward. Each plug connection includes isolated electrical contacts for a test lead. Each signal lead of the test leads is designated by the reference number 10 in FIG. 1, while the reference lead is designated 10'. Each of the test leads 10 and 10' terminates in a plug connection 14, which takes the form of a small sleeve connection and which includes an electrical contact for the associated wire 10 or 10'. Each of the test leads 10 and 10' is connected at the opposite end to an adhesive pad 16 which is attached to the patient to monitor that patient's cardiac activity.

The cable connector 12 includes a plurality of light emitting diode displays 20, one for each signal lead 10. The light emitting diodes 20 are positioned on the cable connector 12 so as to be positionally associated with the particular signal lead 10 which they monitor.

Figure 2:
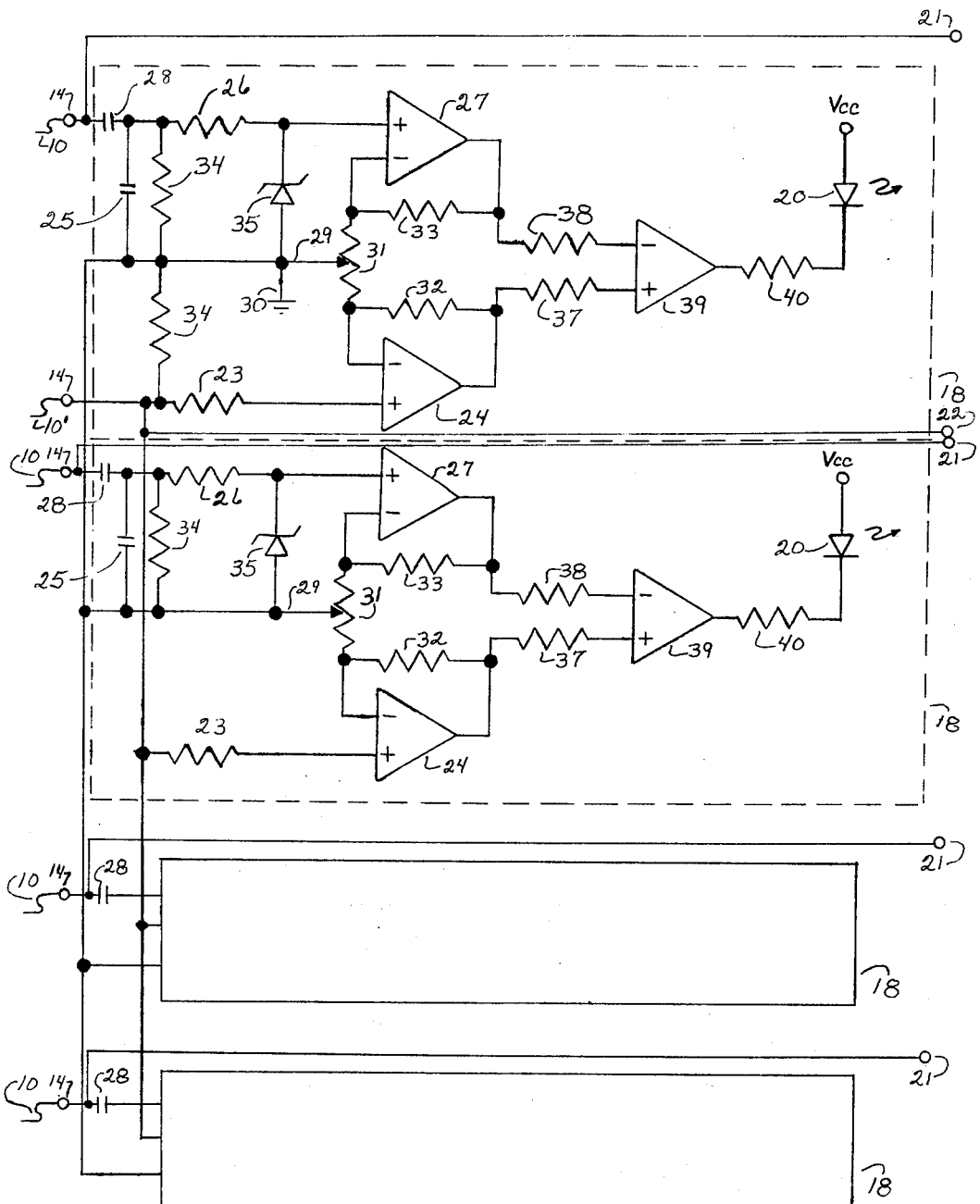
FIG. 2 is a block diagram of the preferred circuitry contained within the connector for operating the LED displays.

The electrical connections housed within the cable connector 12 are depicted in FIG. 2. For simplicity, only two of the several identical monitoring circuits 18 are depicted in complete schematic detail. It is to be understood that the other monitoring circuits 18, illustrated in block form, include identical electrical components to those specifically depicted and described.

As indicated in FIG. 2, each of the signal leads 10 is associated with a common reference lead 10'. The signal and reference leads 10 and 10' respectively are directly connected through the cable connector 12 by the sleeve connections 14 and appear as EKG connection wires 21 and 22, which are housed within the cable 15. It should be noted that they is no break in continuity between the patient and the EKG monitor, and that the cable monitoring circuitry 18 associated with each signal lead 10 operates in parallel across the signal leads 10 and the common reference lead 10'.

The input from the reference lead 10' is fed through a high impedance resistor 23 to the positive terminal of a differential amplifier 24 in the primary amplification stage. The input from the signal lead 10 is connected, through an a.c. coupling capacitor 28 to a filtering network. The filtering network includes a resistor 34 and capacitor 25 connected in parallel with each other and between the signal lead 10 and a floating ground line 29, which is grounded at 30 to the EKG unit. Each signal line 10 is also connected through a high impedance resistor 26 to the positive terminal of a second differential amplifier 27 in the primary amplification stage.

The floating ground line 29 is connected to the wiper of a trimpot 31 which is connected between the negative terminals of both of the differential amplifiers 24 and 27. The trimpot is a factory adjusted balance for 24 and 27. Feedback resistors 32 and 33 from differential amplifiers 24 and 27 respectively are connected to either side of the resistor pot 31. Any change in feedback is therefore reflected as offsetting influences to the negative terminals of the amplifiers 24 and 27.

A zener diode 35 is connected across the inputs to the opposing terminals of the differential amplifier 27 to prevent voltage feedback to the patient. Preferrably, all of the differential amplifiers are operated from a nine volt d.c. supply Vcc. The zener diode 35 forms a voltage input protection circuit on the input side of each signal lead 10 between the signal lead and the floating ground line 29. Should any short circuit develop within the voltage supply to the differential amplifier 27, the zener diode 35 will prevent coupling above a threshold voltage to the patient. For further protection, the capicators 25 and 28 will not allow the passage of d.c. current to the patient. The zener diode 35 thereby clamps the voltage input to the differential amplifier 27 to a value lower than the minimum power supply available.

This zener diode 35 also protects the amplifier inputs expansion needs from being damaged when a patient is being deteriorated. The zener diode 35 therefore protects the input circuitry to the amplifiers from damage when defribilation occurs.

Voltage protection, in the form of connection of the zener diode 35 and the capacitors 25 and 28 and the resistor 34 are provided in association with each signal lead 10. Conventional cable monitoring devices employ voltage protection only at the operating voltage supply and not at the leads to the patient.

By connecting the inputs to the differential amplifiers 24 and 27 in opposition, a guard circuit is provided to prevent interference of ambient 60 cycle noise. In areas where conventional a.c. devices such as the EKG monitor are operated, 60 cycle noise is continually induced through the ambient air at a very low level in electrical components in the vicinity. Because the voltages sensed from the patient on the signal leads 10 are extremely small, this difficulty must be obviated. By connecting the inputs to the differential amplifiers 24 and 27 in the primary amplification stage in opposition, any effects of a.c. noise offset each other. That is, if such effects appear, they appear in both the differential amplifier 24 and in the differential amplifier 27, and in opposition in the two amplifiers.

The outputs of the two primary stage differential amplifiers 24 and 27 are connected respectively through resistors 37 and 38 to opposing inputs of a second stage differential amplifier 39 in each monitoring circuit 18. The output of differential amplifier 39 is through a resistor 40 to an LED 20, depicted both in FIGS. 1 and 2. The output of the LED 20 is connected to the positive supply voltage at 30.

Each monitoring circuit 18 is operated independently of the other monitoring circuits 18, so that any malfunction therein or any break in the signal lead 10 thereto is not reflected in any other monitoring circuit. Thus, if bad connections exist to one electrode pad 16, the LED's 20 associated with the other electrode pads will continue to blink with heartbeat.

It should be noted that the monitoring circuitry 18 of FIG. 2 includes no electrical components for gating. Thus, the primary stage amplifiers 24 and 27 feed the secondary stage amplifier 39 continuously, and are able to detect erractic electron transfers at the surface of the patient's skin to which the test leads 10 and 10' are connected. Also, it should be noted that no pulse shaping circuitry is employed in connection with the monitoring circuitry 18, nor is any external pulse generated therein. This allows the pulses appearing on each signal lead 10 and connected directly through on a wire 21 to the EKG to be used for diagnostic purposes. Also, no threshold detectors are required according to the monitoring circuitry 18. This allows the monitoring circuit to detect voltages as low as 100 microvolts, with consistent reliability.

Input filtering to the monitoring circuitry 18 is provided. Filtering occurs upon reception of signals on signal leads 10 before reaching the inputs to the primary stage differential amplifiers 24 and 27. This allows noise to be filtered from the system before amplification in either the primary or secondary amplifier stages.

The EKG cable monitoring system of the present invention, particularly the presently preferred embodiment depicted in FIG. 2, provides a fast and positive means for determining the proper connection and operation of a plurality of EKG test leads from a patient to the cable connector 12. As previously noted, each LED 20 blinks with the occurrence of a heartbeat, which results in an electron transfer at the surface of the skin of the patient. This electron transfer culminates in a pulse signal on the wire 21, and is referenced against the level on the reference lead 10' in the monitoring circuitry 18. If there is a break in the cable 15 to the EKG monitor, the monitoring circuitry 18 will continue to operate. No CRT trace will appear on the EKG although the LED's 20 will continue to blink with the occurrence of each heartbeat.

If the connection to ground at 30 by the floating ground line 29 is bad, all of the LED's 20 will be illuminated continuously and concurrently. Should the electrode connections in any of the adhesive pads 16 be faulty, or should signal lead 10 to any particular monitoring circuit 18 form an open circuit condition, only the LED 20 associated with that monitoring circuit 18 will be effected. The other monitoring circuits 18 will continue to operate normally.

Should the patient's heartbeat stop, all of the LED's 20 will be extinguished.

While a presently preferred embodiment and alternatives of the EKG monitoring system of the present invention have been described in detail, it should be appreciated that further alternatives to the circuitry are possible and that the scope of the invention is not to be limited except according to the following claims.

What is claimed is:

1. An EKG cable monitoring system for use with a cable assembly having a plurality of test leads connected to a cable connector for a multiconductor cable to an EKG unit and including at least one reference lead and a plurality of signal leads connected to electrodes electrically coupled to the skin of a patient, said system comprising:
    a visual display including a plurality of display devices, each electrically coupled to an associated signal lead and mounted on said cable connector in positional association with the signal lead to which it is coupled; and
    separate display drive means coupled across each signal lead and a reference lead, each drive means comprising a pair of primary differential amplifiers, the combined outputs of which are connected to drive a single one of said display devices, wherein a single one of each of said signal leads is coupled to a single one of said drive means, and therein coupled to a first polarity iput of a first one of said pair of primary differential amplifiers and said reference lead is connected to the first polarity input of the second one of said pair of primary differential amplifiers, and the opposite polarity inputs to said differential amplifiers are connected to a common floating ground.

2. The cable monitoring system defined in claim 1 wherein said visual display means or light emitting diodes.

3. The cable monitoring system of claim 1 further characterized in that in each separate display drive means the outputs of said differential amplifiers are connected to said visual display device, and said signal lead thereto is coupled to the positive input of said first one of said primary differential amplifiers and said reference lead is connected to the positive input of said second one of said primary differential amplifiers, and said negative inputs of said first and second primary differential amplifiers respectively are connected to said floating ground.

4. The cable monitoring system of claim 1 further characterized in that said signal lead is a.c. coupled to an associated one of said drive means.

5. The cable monitoring system of claim 1 further characterized in that high impedance resistances are interposed between said test leads and each of said inputs to said primary differential amplifiers.

6. The cable monitoring system of claim 1 further characterized in that voltage clamping circuits operate between each of said signal leads and said floating ground.

7. The cable monitoring system of claim 1 further characterized in that said reference lead and said signal leads are all filtered from said floating ground.

8. The cable monitoring system of claim 1 further characterized in that each pair of primary differential amplifiers of each display drive means forms a primary amplifier stage having dual differential amplifiers connected in opposing polarity to said signal and reference leads of said test leads associated therewith, and each display drive means further comprises a secondary amplifier stage having a differential amplifier coupled to receive the outputs of said primary amplifier stage in opposition and connected with a secondary stage output to drive said visual display device.

* * * * *